United States Patent [19]

Telford et al.

[11] Patent Number: 4,593,568
[45] Date of Patent: Jun. 10, 1986

[54] ULTRASONIC INSPECTION OF TUBE TO TUBE PLATE WELDS

[75] Inventors: David W. Telford, Thurso; Thomas S. Peat, Halkirk, both of Scotland

[73] Assignee: United Kingdom Atomic Energy Authority, London, England

[21] Appl. No.: 691,002

[22] Filed: Jan. 14, 1985

[30] Foreign Application Priority Data

Jan. 26, 1984 [GB] United Kingdom ............... 8402098

[51] Int. Cl.⁴ ............................................ G01N 29/04
[52] U.S. Cl. ........................................ 73/623; 73/629; 73/640; 376/252
[58] Field of Search ................ 376/249, 252; 73/622, 73/623, 629, 640

[56] References Cited

U.S. PATENT DOCUMENTS

| | | | |
|---|---|---|---|
| 4,117,733 | 10/1978 | Gugel | 73/640 |
| 4,361,044 | 11/1982 | Kupperman et al. | 73/623 |
| 4,474,064 | 10/1984 | Naruse et al. | 376/249 |

Primary Examiner—Howard A. Birmiel
Attorney, Agent, or Firm—William R. Hinds

[57] ABSTRACT

To monitor the deterioration of a weld (10) between a tube (11) and tube plate (12) which has been repaired by a repair sleeve (14) inside the tube and brazed at one end to the tube, ultrasound from a crystal (21) at the end of a rod (24) is launched into the tube through the braze (15) and allowed to travel along the tube to the weld and be reflected back along the tube. The technique may also be used for the type of heat exchanger in which, during construction, the tubes are welded to the tube plate via external sleeves in which case the ultrasound is used in a similar manner to inspect the sleeve/tube plate weld.

10 Claims, 6 Drawing Figures

ULTRASONIC INSPECTION OF TUBE TO TUBE PLATE WELDS

BACKGROUND OF THE INVENTION

This invention relates to the inspection of welds between tubes and tube plates as arise for example in heat exchangers used for steam generation in nuclear reactors. The tubes may be directly welded to the tube plate or, alternatively, indirectly through the agency of an external sleeve.

In the former case, the welds may develop faults such as defect cracks from time to time and a method of repair has become established. The method involves inserting a repair sleeve inside the tube and explosively welding one end of the sleeve to the tube plate and brazing the other end of the sleeve to the inside wall of the tube. This by-passes the weld and superficially removes the faulty weld from any further consideration. However, in practice a requirement exists to monitor or inspect periodically and rapidly the faulty weld as, despite its fault, it nevertheless serves as a back-up for the strength and leak security of the repair sleeve and the behaviour of the defect in this weld indicates the stresses which exist in the assembly and the likely condition of the interspace between the tube and the sleeve. The fact that the weld is now covered by the sleeve makes close access for inspection impossible.

The same considerations arise in the type of heat exchanger where, during construction, the tube is welded to the tube plate via an external sleeve, ie. there is a requirement for the weld to be inspected periodically and, in practice, such inspection must necessarily be carried out from the interior of the tube.

FEATURES AND ASPECTS OF THE INVENTION

The present invention provides a method of inspecting a weld associated with a tube and tube plate assembly in which the tube and a sleeve fit one within the other, the outer one of the sleeve and tube being welded to the tube plate by the weld to be inspected and the sleeve and tube being bonded together, for example by a braze or other bond which is substantially transparent to ultrasound, at a position spaced axially from the weld, said method being characterised by locating an ultrasonic transducer internally of the sleeve and tube, operating the transducer to couple ultrasound into said outer one of the sleeve and the tube through the bond therebetween whereby the ultrasound propagates along said outer one towards said weld, and analysing the reflected ultrasound returning along said outer one and via the bond to detect any ultrasound signal components reflected by flaws in said weld.

It has been found that a good success rate in detecting flaws is obtained if the ultrasound coupled into said outer one is in the form of a Lamb-type wave, especially of a higher order than the fundamental mode. With fundamental mode Lamb waves, the energy distribution tends to be concentrated primarily at the surfaces of the material and such waves therefore tend to be more sensitive to surface defects. With higher order modes, the energy tends to be more uniformly distributed throughout the thickness of the material and consequently the harmonics tend to be more sensitive to defects within the body of the material.

In a preferred embodiment of the invention, the transducer comprises a wedge transducer whose frequency of operation and angle is selected so that Lamb-type waves of higher order than the fundamental mode are excited in the outer one of the tube and the sleeve.

Although the term "Lamb wave" is normally used to refer to acoustic waves with particular characteristics excited in plates, an analogous form of wave with such characteristics can be excited in tube material and is herein referred to as a "Lamb-type" wave. Lamb waves, in contrast with shear waves, interact with opposite surfaces of the medium in which they propagate such that, in effect, the medium with its opposite surfaces forms a waveguide for the acoustic waves. In general, the transition from shear wave transmission to Lamb wave transmission occurs when the wavelength of the acoustic wave is of the order of one tenth the plate thickness or greater. Thus, in the present invention, to secure propogation of Lamb-type waves in the tube material, ie. the tube or sleeve, the acoustic waves generated will typically have shear wavelengths of the order of one tenth the tube or sleeve wall thickness or greater.

DESCRIPTION OF THE DRAWINGS

The invention will now be described further with reference to the accompanying drawings in which.

DESCRIPTION OF THE PREFFERED EMBODIMENTS

Figure 1:
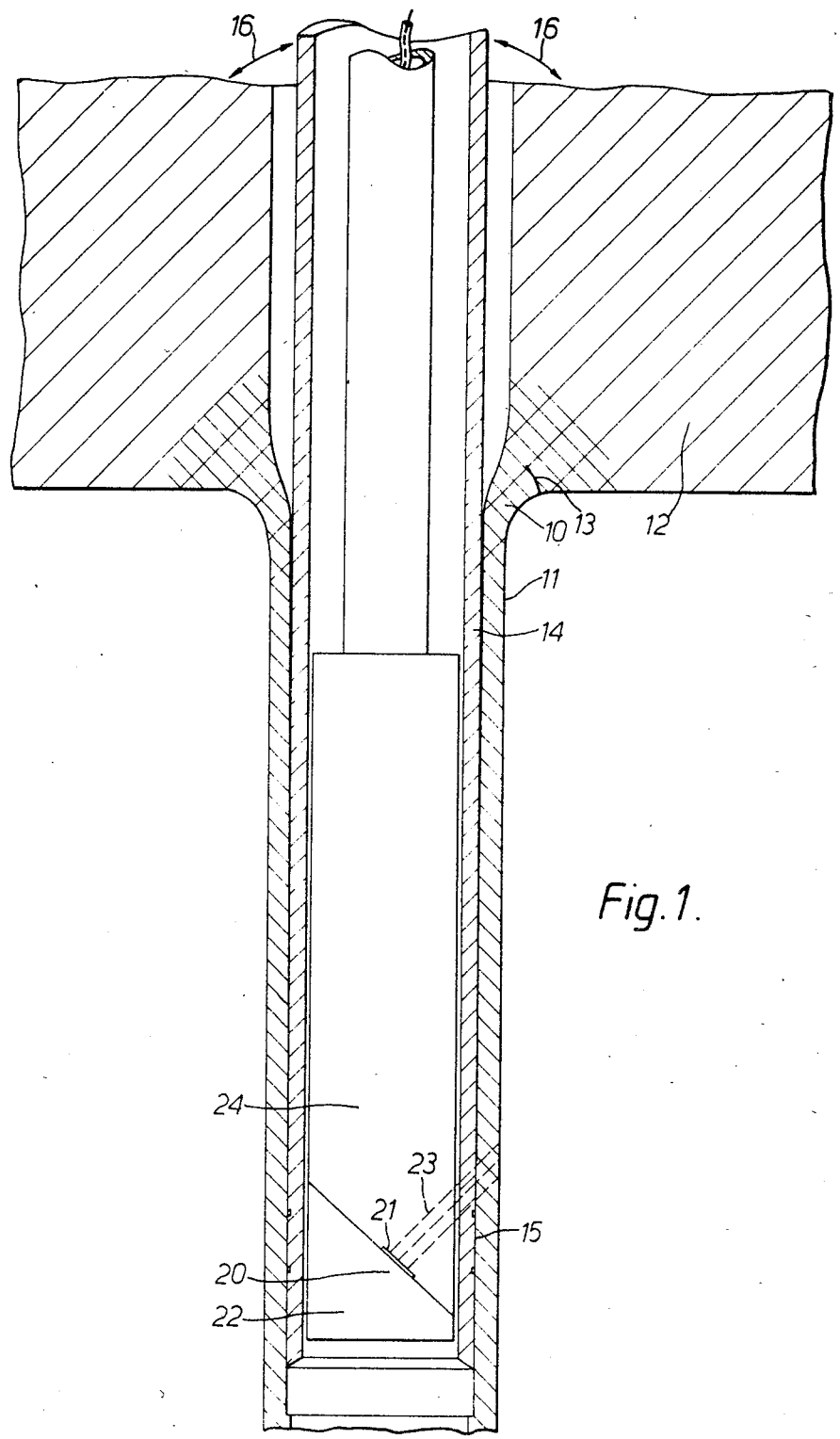
FIG. 1 is a longitudinal section through a tube to tube plate weld following repair.

Referring to FIG. 1, a butt weld 10 is shown between a tube 11 and tube plate 12. The weld has become faulty at a defect crack 13 and has been repaired by a repair sleeve 14 brazed at its lower end (braze 15) to the inside wall of the tube 11 and explosively welded at its upper end to the tube plate 12 (not shown on the drawing as it lies well above the drawing but represented by arrows 16.).

Inside the sleeve 14 there is shown an inspecting ultrasonic head 20 operating in the pulse/echo mode comprising a crystal 21 and acoustic baffle 22. Ultrasound waves from and to the crystal and indicated by dash lines 23. The head 20 is mounted at the wedge end of "PERSPEX" rod 24 which is of a length such that the ultrasound wave represented by lines 23 passes, via a water couplant, through the braze 15 whereupon it enters the tube 11, travels along the tube 11 and tests the weld 10 primarily for circumferentially orientated cracks which reflect the ultrasound back along the tube 11.

By introducing the ultrasound wave into the braze the braze itself causes no significant interference. The long ultrasound path does not cause any serious dispersion or attenuation of signals and the separation of any weld echo from the interface (rod 24 to sleeve 14) signal enhances the signal to noise ration thus enabling more gain to be applied. The wave path along the tube is free from attenuation of the signal due to ultrasound re-radiating into the water couplant as the sleeve 14 isolates the couplant from the tube 11. This increases the amplitude of the signal and provides more sensitivity than would be expected. The head 20 is rotated in steps of about two degrees. Typically it is driven by a stepping motor giving 200 steps per revolution of the head.

Figure 2:
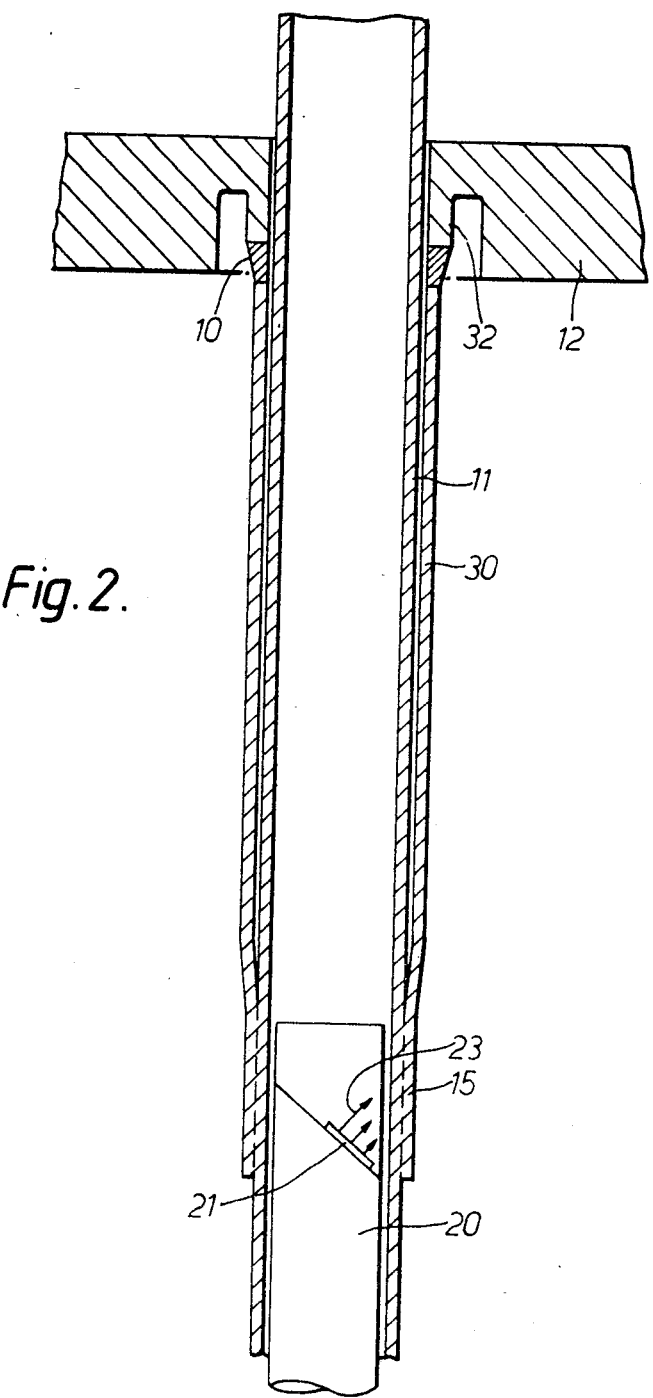
FIG. 2 is a similar view to that of FIG. 1 but showing an alternative arrangement in which the tube is connected to the tube plate via an external sleeve butt welded to the tube plate, like parts being identified by the same reference numerals as in FIG. 1.

FIG. 2 illustrates the alternative arrangement in which the butt weld 10 is between an external sleeve 30 and a pintle 32 formed on the tube plate 12, the sleeve 30 being connected to the tube 11 via the brazed region 15. As in FIG. 1, inspection of the weld is accomplished by launching ultrasound into the outer one of the sleeve and tube (ie. the sleeve 30 in the case of FIG. 2) through the braze.

As mentioned previously, a good success rate in detection of flaws has been achieved by coupling the acoustic energy into the outer one of the sleeve and tube in the form of Lamb-type waves, preferably of higher order than the fundamental mode. The generation of Lamb-type waves is dependent upon the wavelength of the ultrasound in relation to the thickness of the material. Typically Lamb-type waves can be obtained if the ultrasound has a shear wavelength of the order of one tenth the material thickness or greater. Thus, the appropriate wavelength can be obtained by selection of the operating frequency of the cyrstl taking into account the bulk shear velocity of the material. For example, with reference to FIG. 1, where the tube wall thickness is 2.3 mm and the material is a 2.25% Cr, 1% Mo ferritic steel, the bulk shear velocity was calculated to be 3274 m/sec so that, with a crystal frequency of 5 MHz, a shear wavelength of the order of 0.65 mm can be obtained, ie. a shear wavelength between one third and one quarter of the tube wall thickness.

Figure 3A:
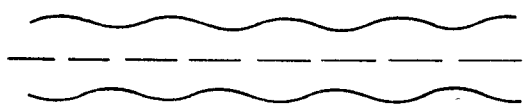
FIG. 3A illustrates a symmetric mode Lamb wave.
Figure 3B:
FIG. 3B illustrates an antisymmetric mode Lamb wave.
Figure 4:
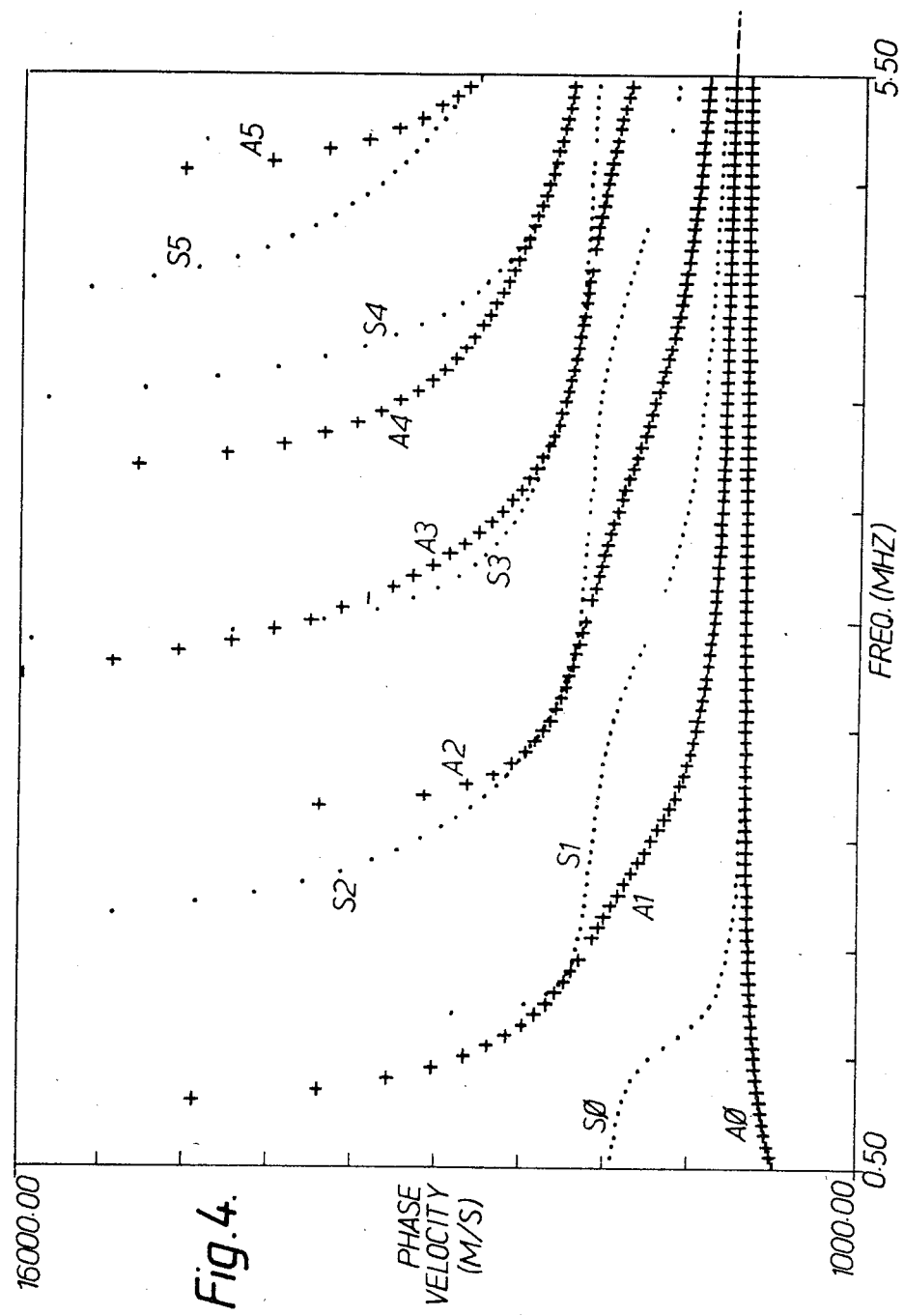
FIG. 4 is a graphical representation of dispersion curves for Lamb waves in a plate.

The selection of the crystal operating frequency is also an important factor in determining which Lamb wave modes are predominantly excited. Another important determining factor in this respect is the wedge angle of the transducer. In practice, Lamb waves can be excited in both symmetrical and antisymmetrical forms as illustrated diagrammatically in FIGS. 3A and 3B respectively and in fundamental and higher order (harmonics) modes. FIG. 4 illustrates a series of dispersion curves for Lamb waves in a plate 2.3 mm thickness and material with a bulk shear velocity of 3274 m.sec$^1$, the abscissa being crystal frequency and the ordinate being the Lamb wave phase velocity in the material. The different modes are designated by S0 (symmetric, fundamental) SI (symmetric, first harmonic), etc., and by A0 (antisymmetric, fundamental), AI (antisymmetric, first harmonic) etc.

A particular mode can be selected by appropriate selection of the crystal frequency and phase velocity. The latter is, in fact, governed by the wedge angle since the phase velocity is related to the Lamb wave length in the tube material which is determined by the relationship:

$$W_R = W_I \sin^{-1} X$$

where $W_R$ is the Lamb wavelength following refraction of the incident ultrasound, $W_I$ is the wavelength of the incident ultrasound passing through the wedge of "PERSPEX" (Registered Trade Mark), and X is the angle of the wedge.

The above formula will be seen to be Snell's Law for a refracted wave travelling in a medium perpendicular to the normal to the surface of the medium, ie. parallel to the axis of the tube or sleeve. Thus, by appropriate selection of the wedge angle X, a desired Lamb wave phase velocity can be obtained which will propagate lengthwise of the tube or sleeve (as the case may be). Moreover, a phase velocity can be achieved which, in conjunction with the crystal operating frequency, will determine the particular mode excited.

In practice, it is not possible to excite a single symmetric or antisymmetric mode especially when using pulsed ultrasound, which wll have a broad frequency spectrum. Ideally, only one mode should be excited but, as this cannot be realised with pulsed ultrasound, it has been found expedient to deliberately select a working point (ie. phase velocity and crystal frequency) located between adjacent dispersion curves so that the corresponding modes are predominantly excited. If the working point is arranged to coincide with a particular dispersion curve, that mode and those immediately above and below it (ie. three modes) will tend to predominate.

In one example of the invention, a "PERSPEX" rod 100 mm long, 95 mm in diameter was truncated at 48°. A 5 MHz PZT crystal was mounted on the truncated face using silver-loaded epoxy resin. The crystal was backed with tungsten-loaded epoxy resin as an acoustic baffle. When used in conjunction with the ferritic steel tube material described above, this wedge angle yielded a Lamb phase velocity of 3600 m/sec and hence a working point of 5 MHz, 3600 m/sec, resulting in excitation of the A2 and SI modes.

The ultrasonic crystal is operated in pulse-echo mode as a transmitter and receiver and is coupled to conventional ultrasonic test equipment including a pulser/receiver and a display for displaying echo amplitude against time in the form of an A-scan on a cathode ray tube. A gate may also be displayed on the screen; the delay and width of the gate being set to emphasise a particular region of the A-scan, ie. the region corresponding to the location of the weld whereby echos emanating from flaws in the weld can be discriminated from those from other potential points of reflection along the paths of travel of the ultrasound. Data collection equipment may also be provided for collection of the echo data for storage purposes and analysis.

In use, the ultrasonic head will be indexed angularly through 360°, eg. in increments of 1.8°, to produce a complete scan of the weld, the extent of defects being indicated by the angles over which the defect amplitude exceeds a predetermined threshold value. Such inspection may be carried out periodically so that the weld integrity can be monitored and any changes in defect extent detected.

Figure 5:
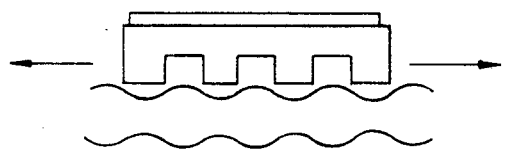
FIG. 5 illustrates diagrammatically an alternative form of transducer.

Although a wedge transducer is preferably employed for exciting Lamb-type waves in the tube or sleeve, other possibilities are feasible. For example, an electromagnetic acoustic transducer (known in the art as an EMAT) may be employed. Such a transducer is illustrated diagrammatically in FIG. 5 and is of the type employing a comb-type pole piece with appropriate energising windings (not illustrated). This transducer may be located adjacent the braze between the tube and sleeve so as to induce an acoustic wave upstream of the overlap between the tube and sleeve. The resulting wave may then diverge at the braze so that a wave travels along both the inner and outer ones of the tube and sleeve (only the wave in the outer one being of interest for present purposes). In this case, the Lamb-type wave is generated by the excitation of normal displacements within the material with a spatial frequency equal to the required Lamb wavelength.

We claim:

1. A method of inspecting a weld associated with a tube and tube plate assembly in which the tube and a sleeve fit one within the other, the outer one of the sleeve and tube being welded to the tube plate by the weld to be inspected and the sleeve and tube being bonded together at a position spaced axially from the weld, said method being characterised by locating an ultrasonic transducer internally of the sleeve and tube, operating the transducer to couple ultrasound into said outer one of the sleeve and the tube through the bond therebetween whereby the ultrasound propagates along said outer one towards said weld, and analysing the reflected ultrasound returning along said outer one and via said bond to detect any ultrasound signal components reflected by flaws in said weld.

2. A method as claimed in claim 1 including coupling the acoustic energy into said outer one in the form of a Lamb-type wave.

3. A method as claimed in claim 2 in which the Lamb-type wave is of higher order than the fundamental mode.

4. A method as claimed in claim 1 in which the transducer is a wedge transducer.

5. A method as claimed in claim 1 in which the transducer comprises an electromagnetic acoustic transducer.

6. A method as claimed in claim 1 including moving the transducer angularly about the axis of the tube so as to couple the ultrasound into said outer one, via said bond, at a plurality of angularly spaced positions whereby a scan of the weld can be made over its entire circumferential length.

7. A method as claimed in claim 1 in which said bond comprises a braze.

8. A method as claimed in claim 1 in which said transducer is operated in the pulse-echo mode and in which the reflected ultrasound signal is gated to discriminate between reflections at the weld and reflections from other sources.

9. A method of inspecting a weld asociated with a tube and tube plate assembly in which the tube and a sleeve fit one within the other, the outer one of the sleeve and tube being welded to the tube plate by the weld to be inspected and the sleeve and tube being bonded together at a position spaced axially from the weld, said method being characterised by:

(a) locating a wedge-type ultrasonic transducer inside the tube and sleeve at a position adjacent said bond;

(b) selecting the working frequency of said transducer and the wedge angle so that ultrasonic energy is transmitted, via said bond, into the outer one of the tube and sleeve in the form of a Lamb-type wave of predetermined order or orders, which wave propagates along said outer one towards said weld; and (c) analysing reflected ultrasound returning from said outer one via said bond to detect any ultrasound signal components reflected by flaws in said weld.

10. A method as claimed in claim 9 in which said Lamp-type wave is of a higher order than the fundamental mode.

* * * * *